US011413281B2

(12) United States Patent
Yu et al.

(10) Patent No.: US 11,413,281 B2
(45) Date of Patent: Aug. 16, 2022

(54) TERNARY CONJUGATE OF ANTITUMOR DRUG, AND SYNTHESIS AND APPLICATION

(71) Applicant: TIANJIN UNIVERSITY OF SCIENCE & TECHNOLOGY, Tianjin (CN)

(72) Inventors: Peng Yu, Tianjin (CN); Na Guo, Tianjin (CN); Dong Wang, Tianjin (CN); Yuou Teng, Tianjin (CN); Tiantian Hao, Tianjin (CN); Huan Liu, Tianjin (CN); Tianle Zhang, Tianjin (CN); Xiuzhuan Shang, Tianjin (CN)

(73) Assignee: TIANJIN UNIVERSITY OF SCIENCE & TECHNOLOGY, Tianjin (CN)

( * ) Notice: Subject to any disclaimer, the term of this patent is extended or adjusted under 35 U.S.C. 154(b) by 209 days.

(21) Appl. No.: 16/089,964

(22) PCT Filed: Jul. 21, 2016

(86) PCT No.: PCT/CN2016/090839
§ 371 (c)(1),
(2) Date: Sep. 28, 2018

(87) PCT Pub. No.: WO2018/010202
PCT Pub. Date: Jan. 18, 2018

(65) Prior Publication Data
US 2019/0358219 A1    Nov. 28, 2019

(30) Foreign Application Priority Data

Jul. 11, 2016  (CN) .......................... 201610542481.8

(51) Int. Cl.
*A61K 31/4745* (2006.01)
*A61K 9/107* (2006.01)
(52) U.S. Cl.
CPC ........ *A61K 31/4745* (2013.01); *A61K 9/1075* (2013.01)
(58) Field of Classification Search
CPC ................................................ A61K 31/4745
See application file for complete search history.

(56) References Cited

U.S. PATENT DOCUMENTS

2005/0186264 A1    8/2005  Kiani et al.

FOREIGN PATENT DOCUMENTS

| CN | 104971353 A | 10/2015 |
|----|-------------|---------|
| CN | 107903389 A | 4/2018 |
| CN | 108578369 A | 9/2018 |
| CN | 108635593 A | 10/2018 |
| CN | 109851773 A | 6/2019 |
| CN | 110124052 A | 8/2019 |
| WO | 2018208700 A1 | 11/2018 |

OTHER PUBLICATIONS

Xu, S. et al., "Synthesis and AChE Inhibitory Activity of Chaicones Mannich Base Derivatives," Chinese J. Org. Chem., 34:749-755 (2013).
Hwang, D.R. et al., "A Modified Mannich-Type Reaction Catalyzed by VO (acac)2," Org Lett., 4(3):749-755 (2013).
An English translation of International Search Report of PCT/CN2016/091979 dated Apr. 26, 2017, WIPO.
Fukuda et al., "A Peptide Mimic of E-Selectin Ligand Inhibits Sialyl Lewis X-dependent Lung Colonization of Tumor Cells," Cancer Research (AACR), 60, pp. 450-456, (2000).
Zhang et al., "Sialyl Lewis X-dependent Lung Colonization of B16 Melanoma Cells through a Selectin-like Endothelial Receptor Distinct from E- or P-Selectin," Cancer Research (AACR), 62, pp. 4194-4198 (2002).
Martens et al., "Peptides Which Bind to E-selectin and Block Neutrophil Adhesion," The Journal of Biological Chemistry, vol. 270, pp. 21129-21136 (1995).
Shamay et al., "E-selectin binding peptide-polymer-drug conjugates and their selective cytotoxicity against vascular endothelial cells," Biomateriais, vol. 30, pp. 6460-6468 (2009).
Shamay et al., "Inhibition of primary and metastatic tumors in mice by E-selectin-targeted polymer-drug conjugates," Journal of Controlled Release, 217, pp. 102-112 (2015).
Han et al., "Free paclitaxel-loaded E-selectin binding peptide modified micelle self-assembled from hyaluronic acid-paclitaxel conjugate inhibit breast cancer metastasis in a murine model," International Journal of Pharmaceutics, vol. 528, pp. 33-46 (2017).
Insug et al., "Peptide Mimicking Sialyl-Lewis with Anti-inflammatory Activity," Biochemical and Biophysical Research Communications, 268, pp. 106-111, (2000).
Insug et al., "Role of SA-Le a and E-selectin in metastasis assessed with peptide antagonist," Peptides 23, pp. 999-1010, (2002).

*Primary Examiner* — James D. Anderson
(74) *Attorney, Agent, or Firm* — Nixon & Vanderhye P.C.

(57) ABSTRACT

Disclosed is a targeted delivery system for a hydrophobic antitumor drug, referring to conjugates of E-selectin polypeptide ligand-polyethylene glycol-antitumor drug connected by different link bridges containing disulfide bonds. The synthesis of the conjugates, antitumor activity evaluation, the particle size and morphology characteristics of nanoparticles self-assembled by the conjugates in an aqueous solution, and the release of the antitumor drug in different conditions are comprised. The conjugates can actively target at vessels of a tumor site by the E-selectin peptide ligand, and can also self-assemble into nanoparticles in an aqueous solution, so as to be passively targeted at the tumor site by EPR effect. The results show that the conjugates have significant antitumor activity but are less toxic to normal cells, can inhibit the adhesion between tumor cells and vascular endothelial cells, have the potential of antitumor metastasis, and have a broad prospect in development and application of antitumor drugs.

14 Claims, 4 Drawing Sheets
Specification includes a Sequence Listing.

TERNARY CONJUGATE OF ANTITUMOR DRUG, AND SYNTHESIS AND APPLICATION

REFERENCE TO SEQUENCE LISTING SUBMITTED ELECTRONICALLY

The content of the electronically submitted sequence listing (Name 6893_0200_ST25.txt; Size: 1,896 bytes: and Date of Creation: Apr. 23, 2021) is incorporated by reference in its entirety.

BACKGROUND

Field

The invention belongs to the field of new compound synthesis and drug application, in particular, to an antitumor ternary conjugate and its synthesis and application, and relates to the synthesis, evaluation and application of a novel glutathione-sensitive amphiphilic conjugate E-selectin peptide ligand-polyethylene glycol-camptothecin alkaloid.

Description of the Related Art

E-selectin can specifically recognize the terminal domains of certain glycoproteins and glycolipid molecules on the surface of leukocytes and tumor cells. Through this recognition, the interaction occurred between E-selectin and leukocytes or tumor cells, then leukocytes or tumor cells start to migrate along the endothelial cells with blood flow, resulting in leukocyte-mediated pro-inflammatory responses and the proliferation and migration of tumor cells, respectively.

The structural characteristics of natural ligand for E-selectin have not yet been fully elucidated. It has been suggested that the identified specific ligands of E-selectin may contain carbohydrates, peptides, and other structural types. The main natural ligand structure currently widely accepted is the tetrasaccharide structure sLex. Theoretically, the specific ligand of E-selectin can be used as a targeting molecule to bring anti-tumor drugs to the tumor site, furthermore, the ligand can also inhibit the migration of tumor cells, therefore the conjugates of E-selectin ligand and anti-tumor drugs are expected to achieve the dual functions of tumor targeting and inhibition of tumor metastasis.

Nanocarriers have been widely used for the transport of anticancer drugs to improve drug solubility and improve the passive targeting of tumors through EPR effect, thereby improving the therapeutic effect. In the preparation of polymer prodrugs, dextran, serum albumin, polyethylene glycol, etc., are usually used as carriers, among which polyethylene glycol possess high hydrophilicity, good biocompatibility, non-toxic and other excellent characteristics. As one of the FDA-approved pharmaceutically acceptable polymers, it is often used to link anticancer drugs and therapeutic proteins to improve drug solubility, bioavailability.

SUMMARY

The object of the present invention is to provide an antitumor ternary conjugate, its synthesis and application, in particular to the synthesis and application of an E-selectin peptide ligand-polyethylene glycol-antitumor drug ternary conjugate, form a ternary conjugate from E-selectin peptide ligand, polyethylene glycol, and hydrophobic antitumor agent, provide a novel anti-tumor drug targeted delivery system, which system can self-assemble into nanomicelles in aqueous solution due to its structural amphiphilic nature, thereby enables passive targeting of tumor sites via the EPR effect, and use E-selectin ligand to active target drugs to tumor neovascularization.

The purpose of the present invention is achieved through the following technical solutions:

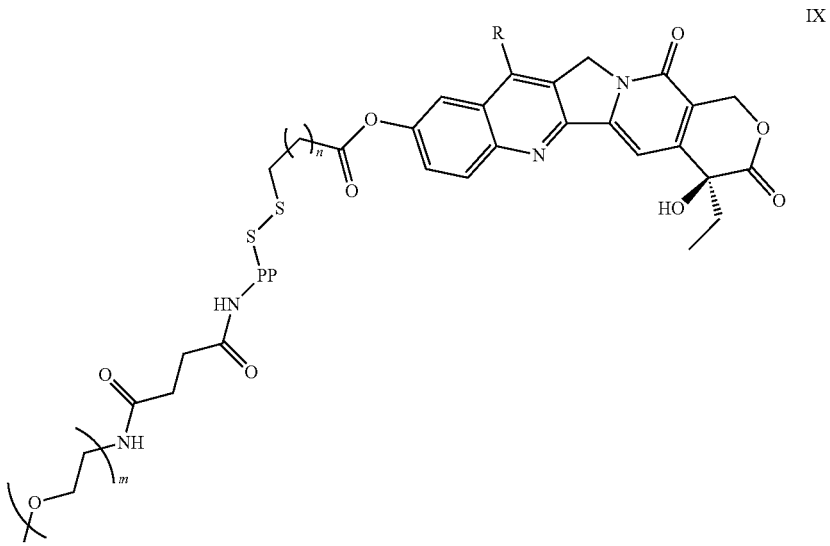

in the structure of antitumor Ternary Conjugate IX, PP is an E-selectin peptide ligand; m=4-1200; n=1-3.
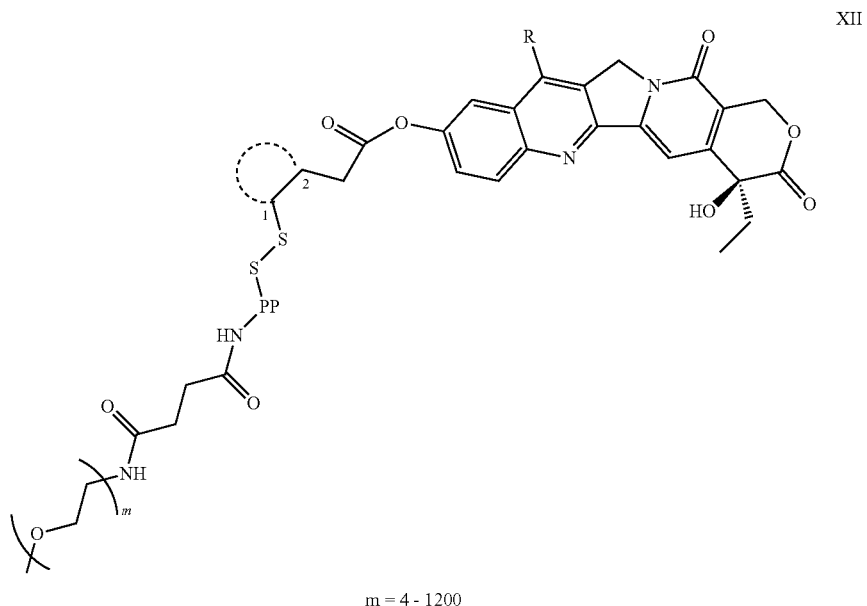
in the structure of antitumor ternary conjugate XII, PP is an E-selectin peptide ligand; m=4-1200; C1 and C2 atoms may be connected to form a 5-7-membered aromatic ring.
The general preparation of Compound IX is as follows:
The general preparation method of Compound XII is as follows:
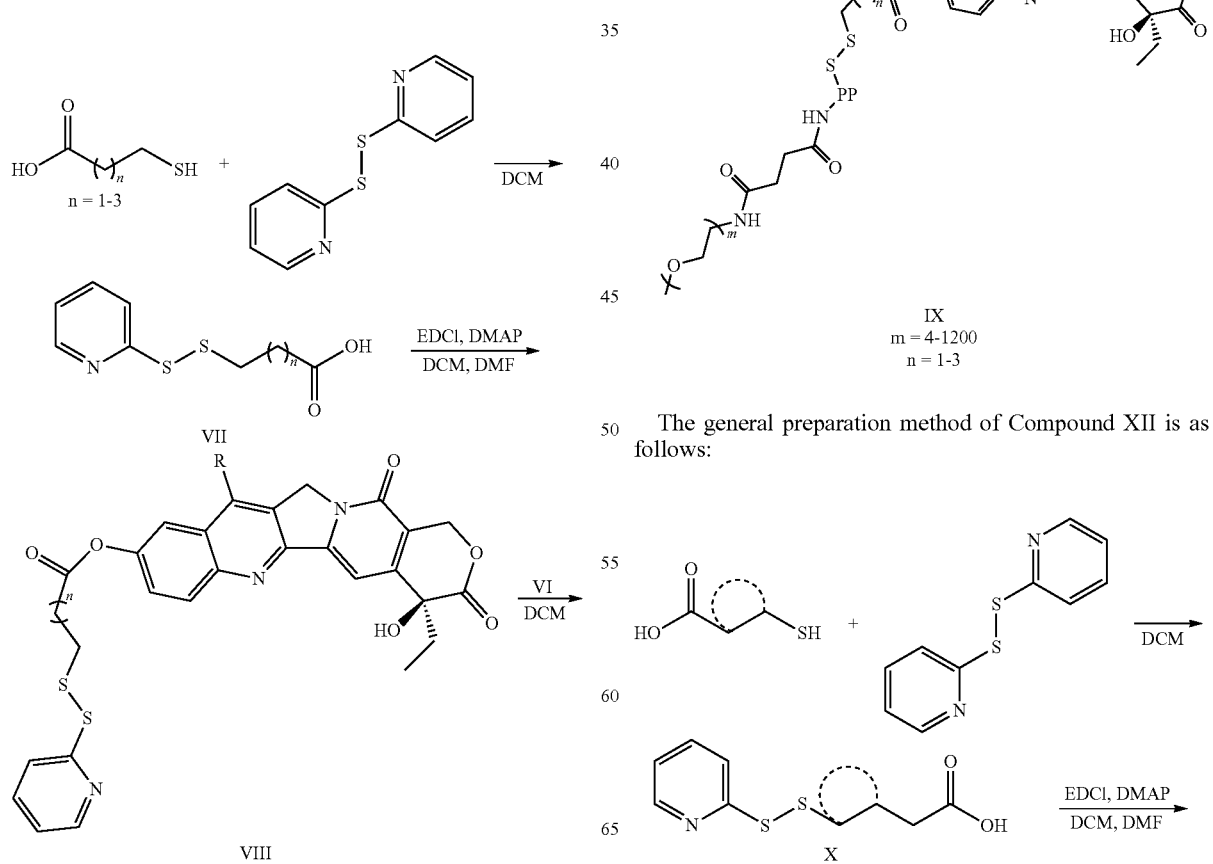

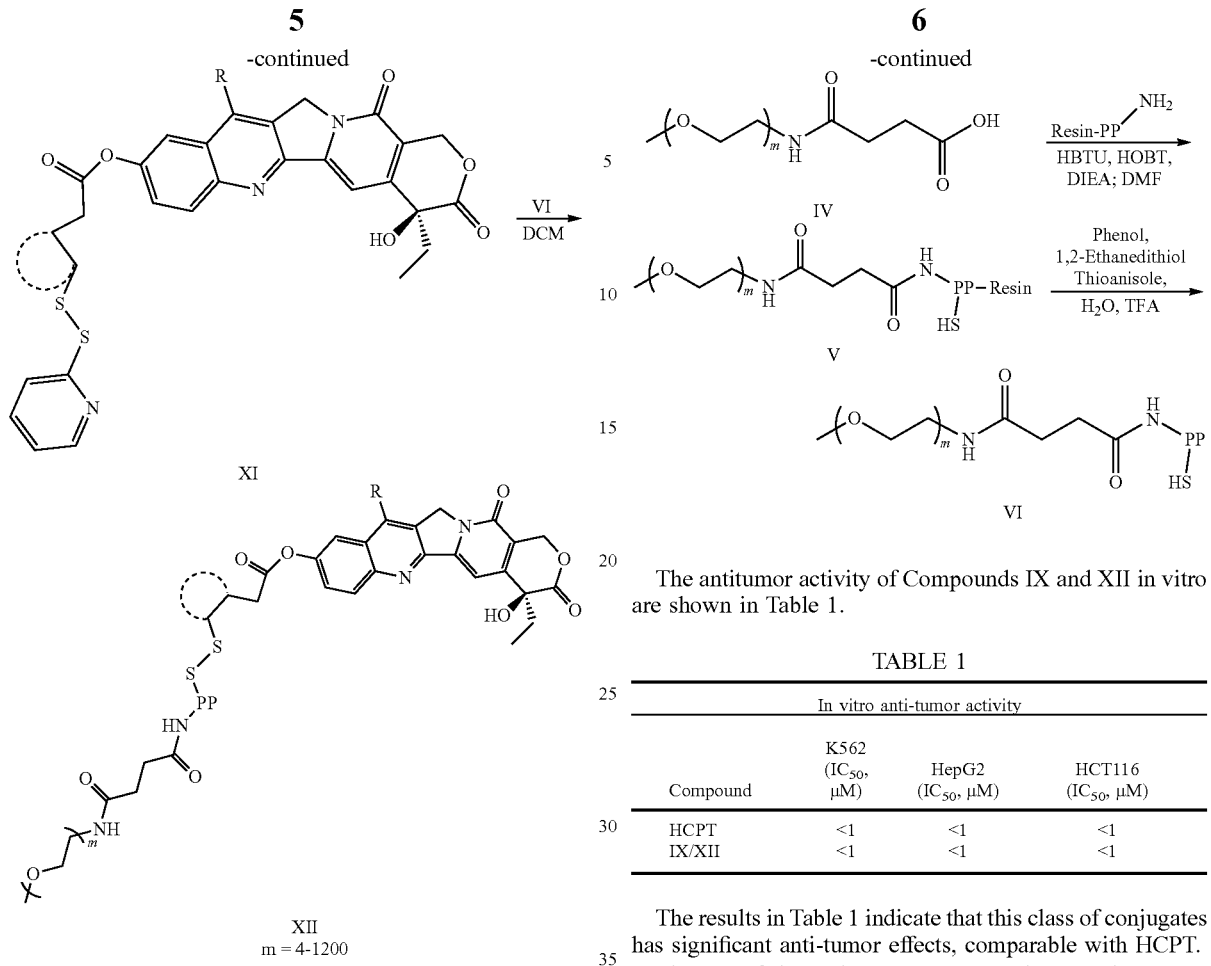

XI

XII
m = 4-1200

Wherein, the molecular weight of mPEG is from 300 to 50,000. The E-selectin peptide ligand PP can be known peptide ligand: IELLQAR (SEQ ID NO: 1), IDLMQAR (SEQ ID NO: 2), DITWDQLWDLMK (SEQ ID NO: 3), DITWDELWKIMN (SEQ ID NO: 4), RNMSWLELW-EHMK (SEQ ID NO: 5), DLWDWVVGKPAG (SEQ ID NO: 6), etc. Antitumor drugs include: camptothecin, hydroxycamptothecin, SN-38 and other hydrophobic antitumor drugs, R is selected from alkyl, alkoxy, or aryl, and the conjugation sites between mPEG-E selectin peptide ligand and the camptothecin antitumor drug include the 10- or 20-hydroxyl position of the camptothecin antitumor drugs and so on.

The synthesis of intermediate VI is as follows:

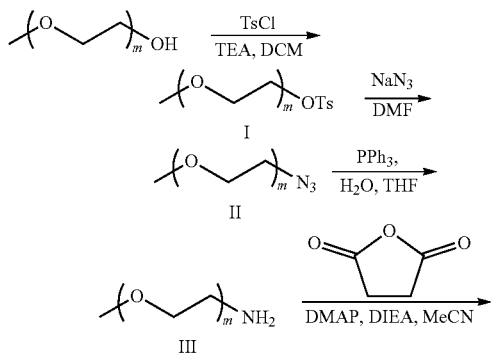

VI

The antitumor activity of Compounds IX and XII in vitro are shown in Table 1.

TABLE 1

| | In vitro anti-tumor activity | | |
|---|---|---|---|
| Compound | K562 (IC$_{50}$, μM) | HepG2 (IC$_{50}$, μM) | HCT116 (IC$_{50}$, μM) |
| HCPT | <1 | <1 | <1 |
| IX/XII | <1 | <1 | <1 |

The results in Table 1 indicate that this class of conjugates has significant anti-tumor effects, comparable with HCPT.

The use of the antitumor ternary conjugates above as a targeted drug delivery system.

The above targeted drug delivery system is an anti-tumor drug delivery system.

In the above system, the conjugate self-assembles into nano-micelles in an aqueous solution through its amphiphilic structure, thereby passively target the tumor site through the EPR effect.

The use of the antitumor ternary conjugates above in the manufacturing of a medicament for the treatment or inhibition or inhibiting metastasis.

The advantages and potential effects of the present invention are as follows:

1. The drug delivery system involved in the present invention is simple in synthesis and suitable for a variety of hydrophobic anti-tumor drugs.

2. By introducing the hydrophilic PEG, it not only enables the conjugated drug to self-assemble into nanoparticles in an aqueous solution, but also passively targets the tumor site through the EPR effect, and meantime it can improve the solubility of the drug, prolong the circulation time in the body, enhance bioavailability, and so on.

3. Through introducing E-selectin peptide ligand, the present invention can actively target the drug to tumor site neovascularization, reduce the toxicity of the drug to normal tissues. In addition, the drug can exert its killing effect on tumor neovascularization and adjacent tumor cells at the same time, and it is expected to obtain better therapeutic effects.

4. In addition to the tumor targeting effect, the E-selectin peptide ligand in the present invention can also inhibit the adhesion between tumor cells and vascular endothelial cells, thereby inhibiting the metastasis of tumor cells.

DETAILED DESCRIPTION

Figure 1:
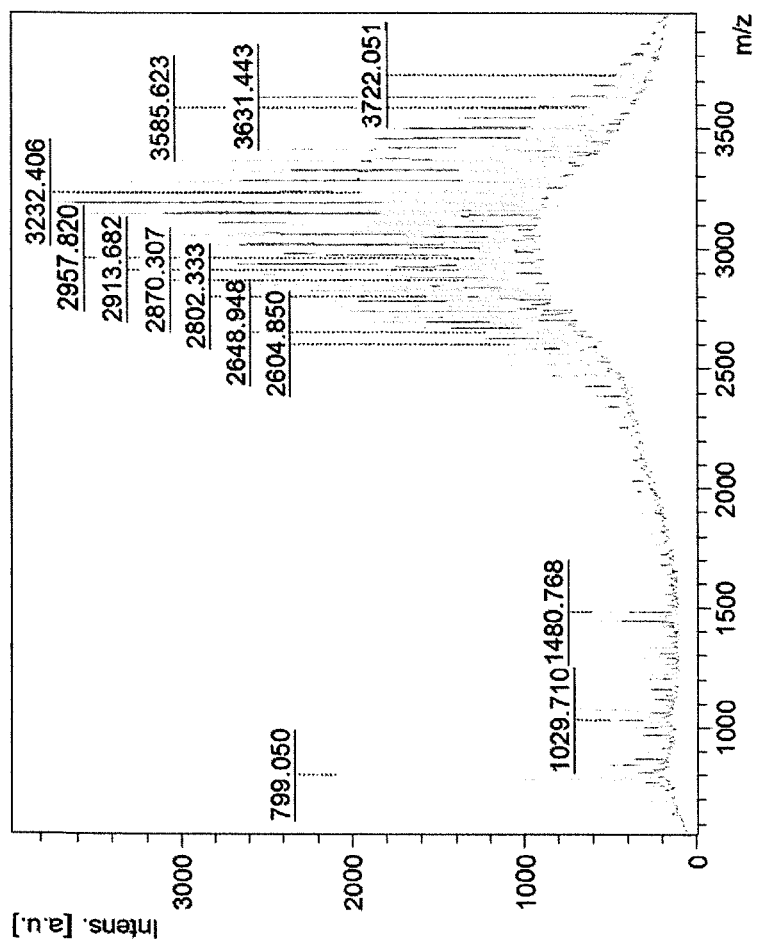
FIG. 1 is the MALDI-TOF spectrum of compound 9.

In order to understand the present invention, the following further describes the present invention in combination with the embodiments: The following examples are illustrative but not restrictive, and the scope of protection of the present invention cannot be limited by the following examples.

The purpose of the present invention is to provide a novel antitumor drug targeted delivery system through coupling an E-selectin peptide ligand, a polyethylene glycol, and a hydrophobic anti-tumor drug. The conjugate can self-assembly into nanomicelles in aqueous solution, thereby achieving passive targeting to the tumor site through the EPR effect, and the E-selectin ligands can actively target the drug to tumor neovascularization because of the over expression of E-selectin on the surface of tumor neovascular endothelial cells. On the other hand, after the conjugate reaches the tumor site, the connecting bridge designed by the present invention can be cut off by a high concentration of glutathione (GSH) in the tumor microenvironment, releasing the original drug to kill the tumor neovascular endothelial cells and the adjacent tumor cells, furthermore, E-selectin ligands can also block or inhibit tumor cell migration by competing with tumor cells for binding to E-selectin. In summary, the targeted drug delivery system has the advantages of dual targeting mechanisms (passive and active targeting), dual tumor growth inhibition mechanisms (inhibiting tumor neovascularization and adjacent tumor cells growth), and dual therapeutic effects (inhibition of tumor growth and tumor metastasis). There is a huge potential for the new applications of hydrophobic anti-tumor drugs.

An antitumor ternary conjugate, characterized in that the ternary conjugate is E-selectin peptide ligand-PEG-antitumor drug, wherein the E-selectin peptide ligand is IELLQAR (SEQ ID NO: 1), IDLMQAR (SEQ ID NO: 2), DITWDQLWDLMK (SEQ ID NO: 3), DITWDELWKIMN (SEQ ID NO: 4), RNMSWLELWEHMK (SEQ ID NO: 5), or DLWDWVVGKPAG (SEQ ID NO: 6), the antitumor drugs include: camptothecin, hydroxycamptothecin or SN-38, the conjugation sites between PEG-E selectin peptide ligand and the camptothecin antitumor drug include the 10-position or 20-position of camptothecin-like drugs.

The E-selectin ligand IELLQAR (SEQ ID NO: 1), was synthesized using a classical solid-phase Fmoc strategy using 2-Chlorotrityl Chloride Resin, and cysteine (C) was added at one end as a linker to get octapeptide $NH_2$-CIELLQAR-COOH (SEQ ID NO: 7).

The synthesis methods of the conjugates IX and XII are basically the same, and the schematic structure of one of the target conjugates is as follows:

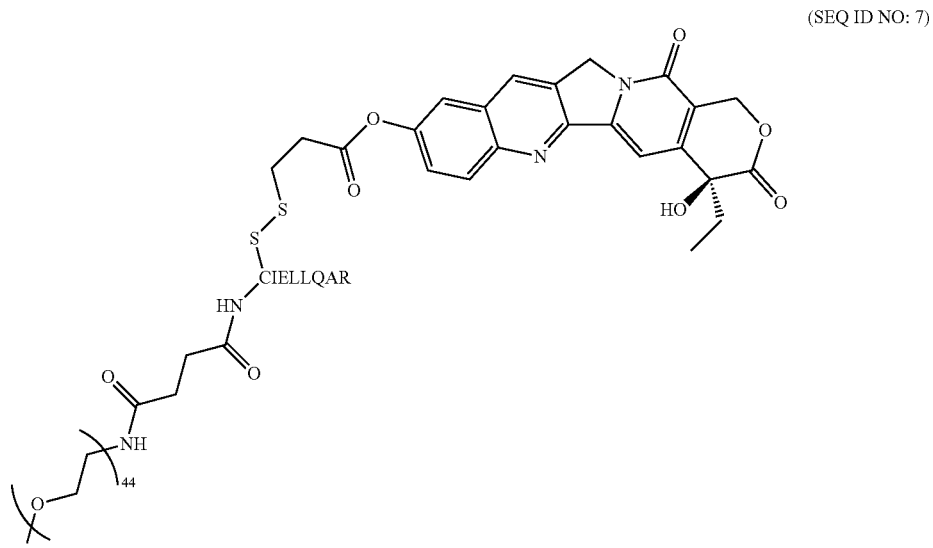

(SEQ ID NO: 7)

In some embodiments of IX, the method of preparation includes the following steps:

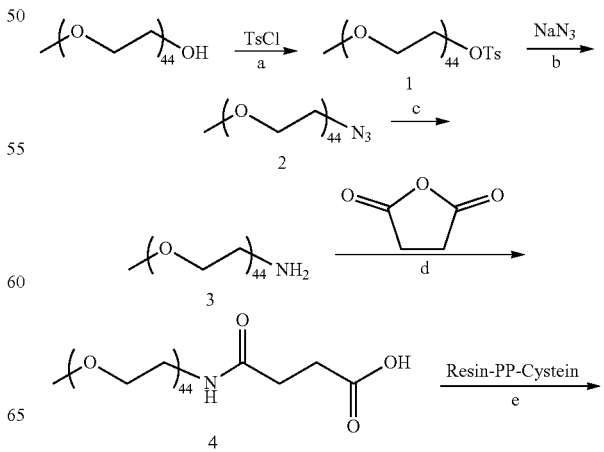

-continued

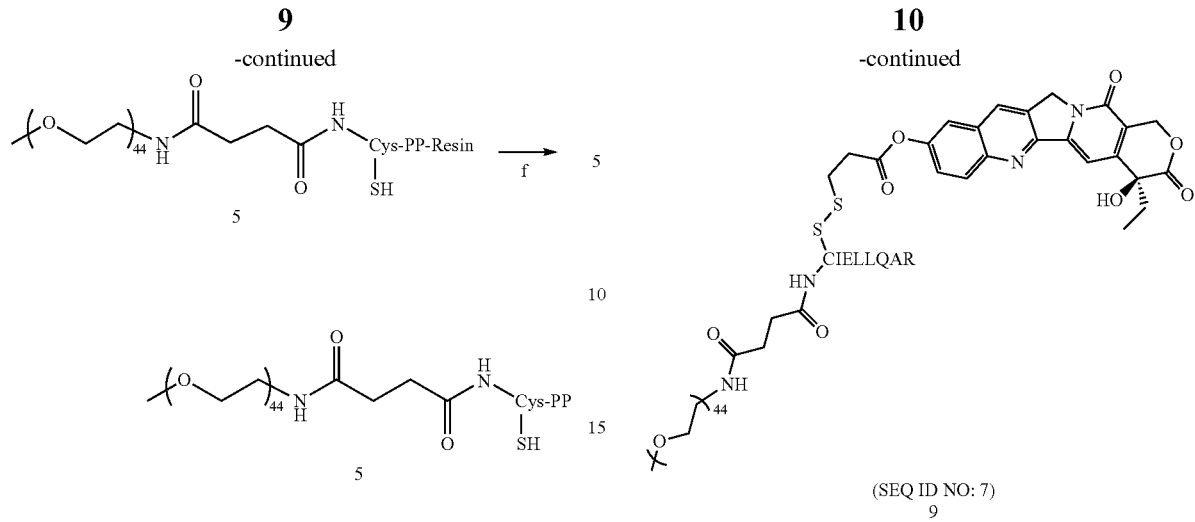

PP is IELLQAR (SEQ ID NO: 1)

Reagents: (a) TEA, DCM; (b) DMF; (c) PPh₃, H₂O, THF; (d) DMAP, DIEA, MeCN; (e) HBTU, HOBT, DIEA; DMF; (f) Phenol, 1,2-Ethanedithiol, Thioanisole, H₂O, TFA.

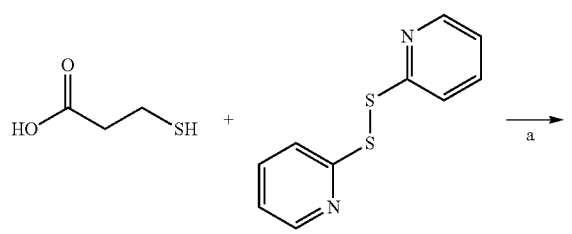

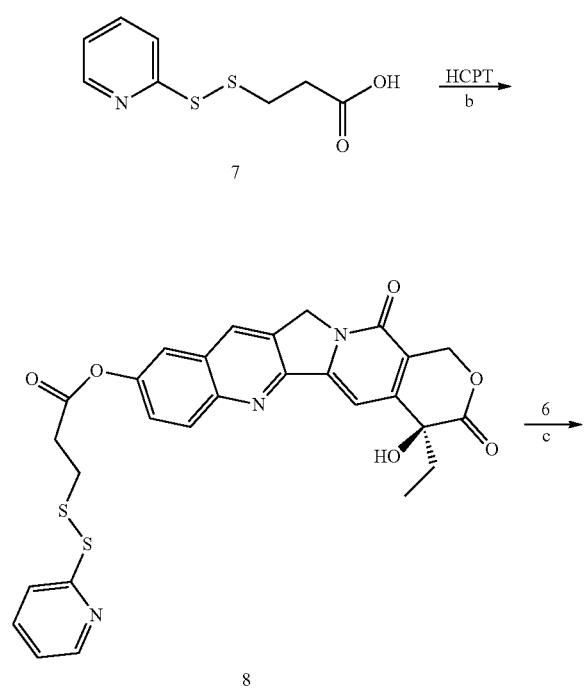

-continued (SEQ ID NO: 7)
9

Reagents: (a) DCM; (b) EDCI, DMAP, DCM, DMF; (c) DCM.

(1) Synthesis of Compound 1

5 g (2.5 mmol) of polyethylene glycol monomethyl ether 2000 was added into 15 ml of anhydrous dichloromethane, then 1.43 g (7.5 mmol) of p-toluenesulfonyl chloride and 2.1 ml (15 mmol) of triethylamine were added under ice bath, react at room temperature overnight. The reaction was monitored by TLC. The reaction solution was diluted with dichloromethane and washed twice with saturated ammonium chloride solution. The organic phases were combined and washed with saturated brine, dried over anhydrous sodium sulfate, and the dichloromethane was removed under reduced pressure. Recrystallization with ether gave 5.1 g compound 1 of a white powder with a yield of 94%.

$^1$H NMR (400 MHz, DMSO-$d_6$) δ (ppm): 7.78 (d, J=8.0 Hz, 2H), 7.48 (d, J=8.0 Hz, 2H), 4.11 (t, J=4.4 Hz, 2H), 3.51 (s, mPEG), 3.24 (s, 3H), 2.44 (s, 3H).

Synthesis of Compound 2

10.2 g (4.7 mmol) of compound 1 was dissolved in 50 ml of anhydrous N, N-dimethylformamide, then 1.85 g (28.2 mmol) of sodium azide was added under an ice bath, and react at 60° C. for 24 hours. The reaction solution was diluted with dichloromethane, washed with saturated brine and water, dried over anhydrous sodium sulfate, remove the solvent under vacuum, re-crystallized with ether to give 8.6 g. compound 2 of white powder with 89% yield.

$^1$H NMR (400 MHz, DMSO-$d_6$) δ (ppm): 3.61 (t, J=5.2 Hz, 2H), 3.52 (s, mPEG), 3.25 (s, 3H).

Synthesis of Compound 3

3.8 g (1.9 mmol) of compound 2 was dissolved in 20 ml of tetrahydrofuran, 0.97 g (3.8 mmol) of triphenylphosphine and 1.7 ml (95 mmol) of water were added, react at 45° C. overnight. The reaction mixture was diluted with water and extracted three times with ethyl acetate. The aqueous phase was collected and extracted six times with dichloromethane. The organic phase was washed with saturated brine, dried over anhydrous sodium sulfate, and evaporated under reduced pressure. Recrystallization with ether gave 3.2 g compound 3 of a white powder with a yield of 85%.

$^1$H NMR (400 MHz, DMSO-d$_6$) δ (ppm): 3.51 (s, mPEG), 3.24 (s, 3H).

Synthesis of Compound 4

3.8 g (1.9 mmol) of compound 3, 0.48 g (4.8 mmol) of succinic anhydride, 0.06 g (0.5 mmol) of 4-dimethylaminopyridine, 0.95 ml (5.7 mmol) of N,N-Diisopropylethylamine were added in 16 ml of acetonitrile, reacted at 60° C. for 2 hours. The reaction solution was diluted with dichloromethane and washed with saturated ammonium chloride solution and saturated brine. The organic phases were combined, dried over anhydrous sodium sulfate, and the dichloromethane was evaporated under reduced pressure. Compound 4 (3 g) was obtained with column chromatography (CH$_2$Cl2: CH$_3$OH=100:1) and ether recrystallization (yield 76%).

$^1$H NMR (400 MHz, DMSO-d$_6$) δ (ppm): 12.05 (s, 1H), 7.91 (t, J=5.6 Hz, 1H), 3.51 (s, mPEG), 3.24 (s, 3H), 3.20-3.16 (m, 2H), 2.40 (m, 2H), 2.31 (m, 2H).

Synthesis of Compound 5

0.2 g (0.17 mmol) of octapeptide-resin was added into 4 ml of N, N-dimethylformamide, then 1.42 g (0.68 mmol) of compound 4, 0.26 g (0.68 mmol) of benzotriazole-,N,N',N'-tetramethyluronium hexafluorophosphate, 0.09 g (0.68 mmol) 1-hydroxybenzotriazole, 0.2 ml (1.4 mmol) N,N-diisopropylethylamine were added, reacted at 28° C. for 2 hours. Once the reaction was completed, the mixture was washed successively with 10 ml of N,N-dimethylformamide, isopropyl alcohol, and N,N-dimethylformamide, giving compound 5.

(6) Synthesis of Compound 6

Lysate Preparation:
Phenol: 1,2-Ethanedithiol:Thioanisole:Water:Trifluoroacetic acid (V/V)
5:5:2.5:5:82.5
0.68 g (0.58 mmol) of compound 5 was added to a 6 ml lysate in an ice bath and reacted at 30° C. for 2 hours. The reaction solution was filtered into cold ether and refrigerated overnight. After centrifugation, the resulting solid was washed three times with ether and dried with argon to give 50 mg of a white powder in a 40% yield.

Synthesis of Compound 7

6.2 g (28.2 mmol) of 2, 2'-dithiodipyridine dissolved in 20 ml of dichloromethane was added 0.42 ml (9.4 mmol) of mercaptopropionic acid in 60 ml of dichloromethane under an ice bath. Then the reaction solution was diluted with dichloromethane, washed with saturated brine and water 6 times, and the organic phases were combined and dried over anhydrous sodium sulfate, and evaporated under reduced pressure. Compound 7 was purified by column chromatography using petroleum ether:ethyl acetate=3:1, to give 1.3 g of compound 7 in a 64% yield.

$^1$H NMR (400 MHz, CDCl$_3$) δ (ppm): 10.54 (s, 1H), 8.47 (t, J=1.2 Hz, 1H), 7.65 (m, 2H), 7.16-7.12 (dd, 1H), 3.05 (t, J=6.8 Hz, 2H), 2.79 (t, J=6.8 Hz, 2H).

Synthesis of Compound 8

0.3 g (0.8 mmol) of 10-hydroxycamptothecin was dissolved in 10 ml of N,N-dimethylformamide, and 0.27 g (1.2 mmol) of compound 7, 0.17 g (1.4 mmol) of 4-dimethylaminopyridine, 0.36 ml (2 mmol) of N,N-diisopropylethylamine were added, then 0.3 g (1.6 mmol) of 1-(3-dimethylaminopropyl)-3-ethylcarbodiimide hydrochloride in a solution 10 ml of dichloromethane was added dropwise to the system and allowed to react at room temperature for 2.5 hours. The reaction solution was diluted with dichloromethane and washed with saturated ammonium chloride solution and saturated sodium bicarbonate solution. The organic phases were combined, washed with saturated brine, dried over anhydrous sodium sulfate, Dichloromethane was evaporated under vacuum. The compound 8 was purified by column chromatography with dichloromethane:methanol=75:1. Recrystallization from petroleum ether gave compound 8 (0.3 g) of a white powder with a yield of 68%.

$^1$H NMR (400 MHz, DMSO-d$_6$) δ (ppm): 8.69 (s, 1H), 8.54-8.49 (m, 1H), 8.22 (d, J=9.1 Hz, 1H), 7.90 (d, J=2.5 Hz, 1H), 7.87-7.80 (m, 2H), 7.69-7.64 (m, 1H), 7.36 (s, 1H), 7.30-7.25 (m, 1H), 6.57 (s, 1H), 5.44 (s, 2H), 5.30 (s, 2H), 3.24 (t, J=7.0 Hz, 2H), 3.13 (t, J=6.4 Hz, 2H), 1.94-1.81 (m, 2H), 0.89 (t, J=7.2 Hz, 3H).

Synthesis of Compound 9

0.14 g (0.25 mmol) of compound 8 in 2.5 ml of anhydrous dichloromethane was added with 0.15 g (0.05 mmol) of compound 6 in 50 ml of anhydrous methylene chloride in an ice bath, then dichloromethane was evaporated, diluted with water, extracted with ethyl acetate. The aqueous phase was collected and extracted with dichloromethane. The dichloromethane phases were combined, washed with saturated brine, dried over anhydrous sodium sulfate, and evaporated under reduced pressure. The mixture was purified on a Sephadex column and lyophilized to give compound 9 (50 mg) of light yellow powder with a yield of 30%. The purity was 95% by HPLC. The MALDI-TOF results are consistent with theoretical molecular weight shown in FIG. 1.

Figure 2:
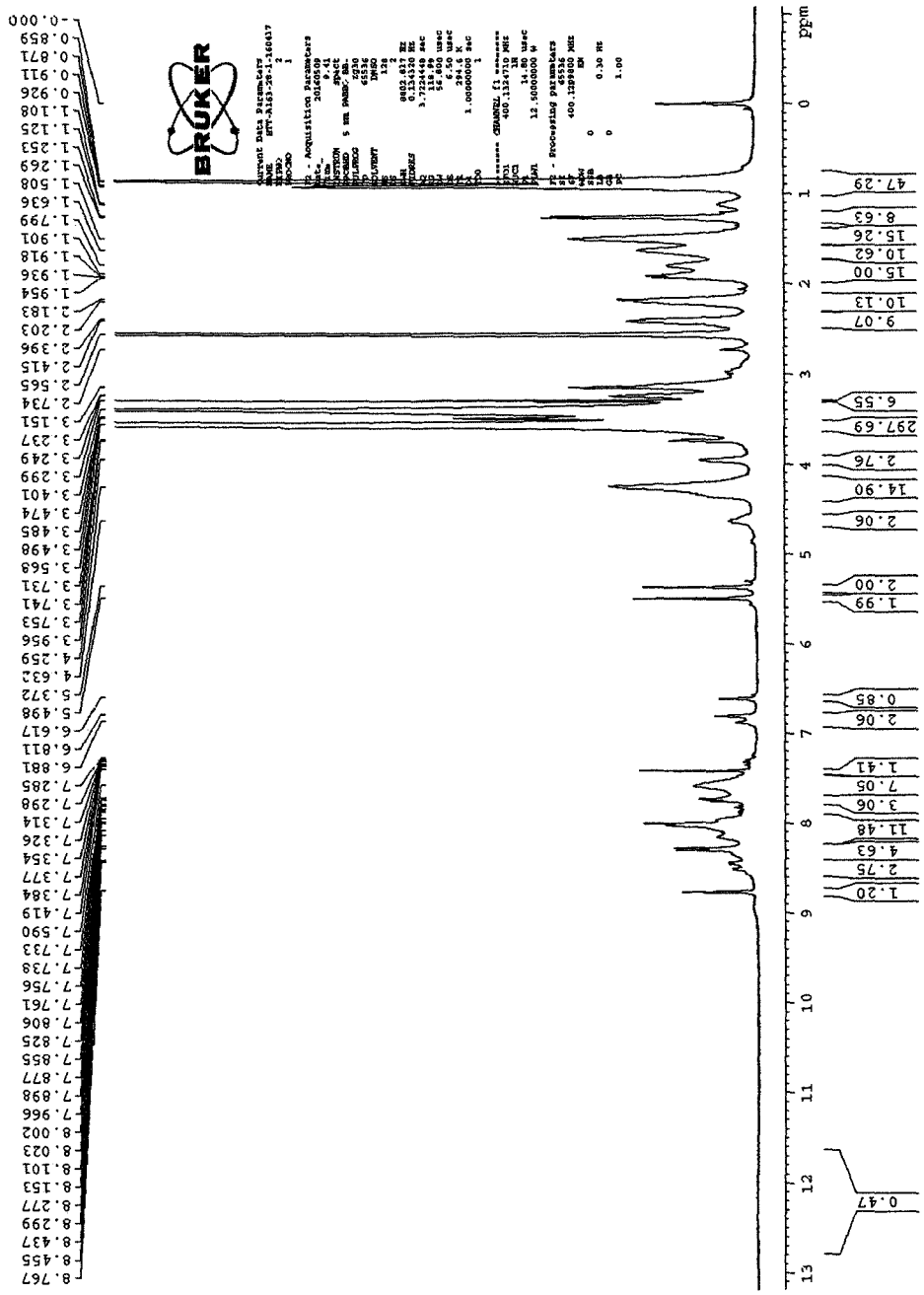
FIG. 2 is a nuclear magnetic hydrogen spectrum of compound 9 in deuterated dimethyl sulfoxide.
Figure 3:
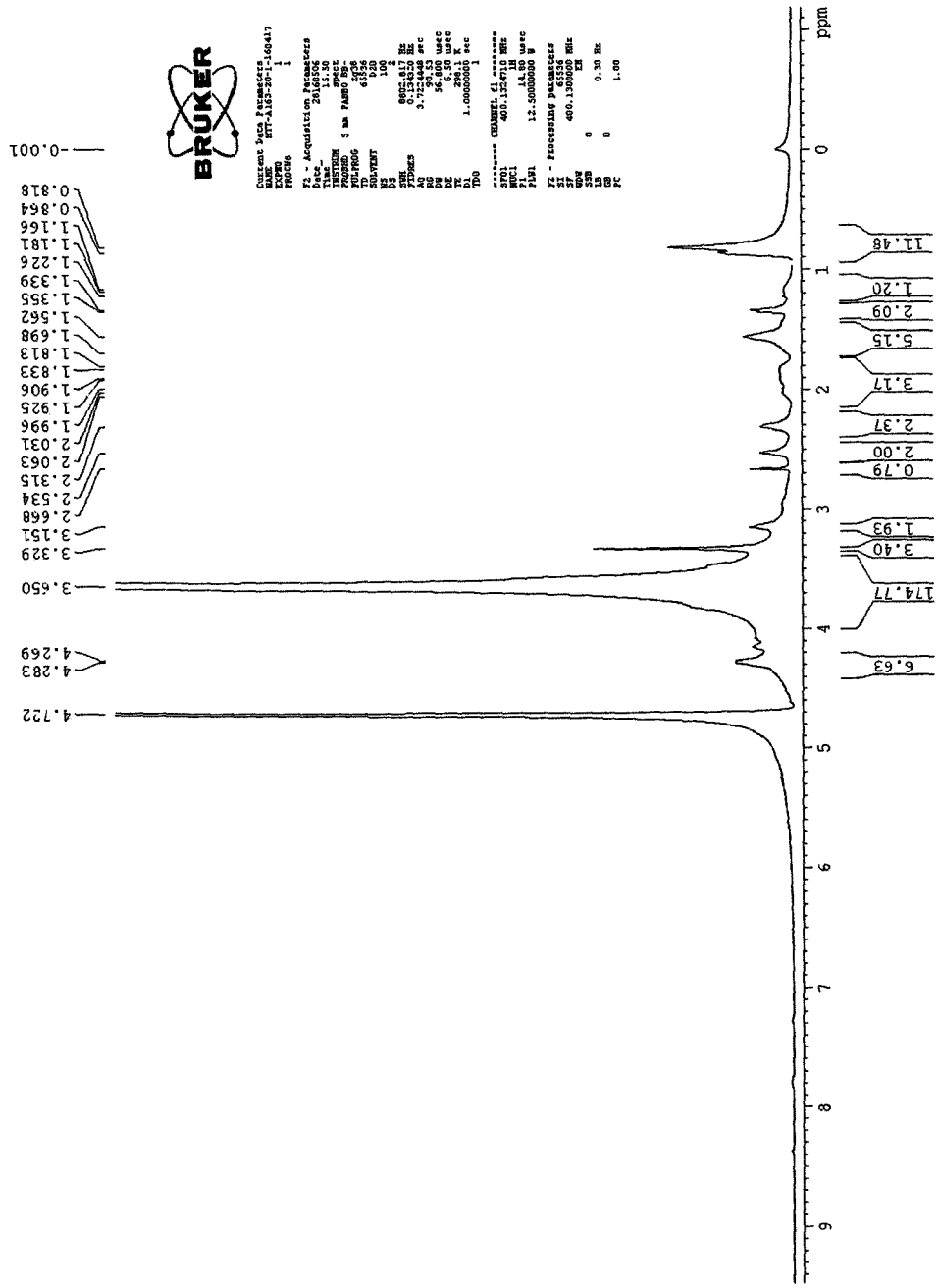
FIG. 3 shows the NMR spectrum of compound 9 in $D_2O$.

The nuclear magnetic proton spectrum of compound 9 is shown in FIG. 2 and FIG. 3, and it can be found that the signals of HCPT disappears in the aqueous solution, the reason is that compound 9 is an amphiphilic structure and can self-assembled into nano-micelles in an aqueous solution. The micelles enclose the hydrophobic structure inside. This result is consistent with our previous study of PEG and HCPT conjugates. This phenomenon also exists in the conjugate of PEG and HCPT, and it is confirmed by dynamic light scattering and transmission electron microscopy, which showing it can form nanospheres or nanorods with about 200 nm diameter.

Figure 4:
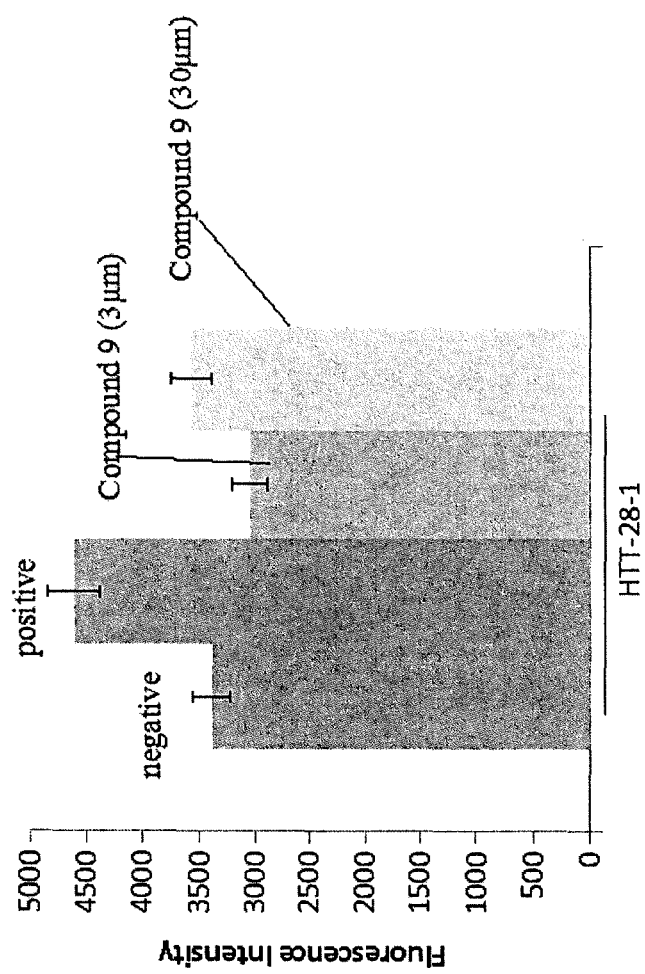
FIG. 4 shows the results of the anti-adhesion of Compound 9 against THP-I and HUVECs (ATCC) in vitro.

As shown in FIG. 4, Compound 9 also showed significant anti-E-selectin mediated cell adhesion in vitro, indicating that the conjugate could also interact with E-selectin.

Example 2. Anti-Tumor Activity Assay

Solution Preparation
Formulation of DMEM low glucose medium: HyClone MEM low glucose medium, 500 mL per bottle, add 10% fetal bovine serum and 1% solution of penicillin, stored in a refrigerator at 4° C.

Preparation of DMEM/F-12 culture broth: HyClone MEM/F-12 medium, 500 mL per bottle, add 10% fetal bovine serum and 1% solution of penicillin, stored in a refrigerator at 4° C.

Preparation of PBS buffer: In a 1000-mL flask, 8 g of sodium chloride, 0.2 g of potassium chloride, 2.9 g of disodium hydrogen phosphate dodecahydrate 2.9 g, potassium dihydrogen phosphate 0.2 g, were added into 800 ml purified water, after stirring and dissolving, the volume was adjusted to 1000 mL, sterilized and stored at 4° C.

Preparation of MTT solution: MTT dry powder 0.5 g was dissolved in 100 mL PBS buffer, filtered and sterilized with a 0.22 µM filter, and placed in a refrigerator at −12° C. for storage.

Three types of tumor cells used in the assay for antitumor activity are human hepatoma cells (HepG2), leukemia cells (K562) and human colon cancer cells (HCT116).

Human Hepatocarcinoma Cell (HepG2) Test

The culture medium for HepG2 cells was DMEM cell culture medium containing 1% penicillin-streptomycin solution and 10% fetal bovine serum, and the culture condition was 37° C. and a constant temperature incubator containing 5% $CO_2$. Specific steps:

The cells were counted using a hemocytometer and diluted with DMEM low glucose to $5\times10^4$ cells/mL.

Add 100 µL of cell suspension to each well of a 96-well plate, mix, incubated at 37° C. for 24 h.

The desired test compounds were diluted to 5 concentrations: 2 mM, 0.2 mM, 20 µM, 2 µM, 0.2 µM, and 0.5 µL/well was sequentially added according to the concentration, incubated at 37° C. for 48 h.

MTT was added at a concentration of 5 mg/mL, incubated at 37° C. for 4 h.

Cells were lysed by addition of DMSO, and the OD values at 490 nm and 630 nm were measured with a microplate reader.

Processing data, calculate $IC_{50}$ value according to OD value.

Human leukemia K562 test

K562 cells were cultured in RPMI1640 cell culture medium containing 1% penicillin-streptomycin solution, 10% fetal bovine serum, and incubated at 37° C. in a constant temperature incubator containing 5% $CO_2$. Specific steps:

The cells were counted using a hemocytometer and diluted to $5\times10^4$ cells/mL with RPMI medium;

100 µL of cell suspension was added to each well of a 96-well plate, incubated at 37° C. for 2 h.

The desired test compounds were diluted to 5 concentrations: 2 mM, 0.2 mM, 20 µM, 2 µM, 0.2 µM, and 0.5 µL/well was sequentially added according to the concentration, incubated at 37° C. for 48 h.

MTT was added at a concentration of 5 mg/mL, incubated at 37° C. for 4 hours.

Isopropanol and hydrochloric acid lysis were added, and the OD values at 570 nm and 630 nm were measured with a microplate reader.

Processing data, calculate $IC_{50}$ value according to OD value.

Human colon cancer cell HCT116 test

The culture fluid used for HCT116 cells was a DMEM/F-12 cell culture solution containing 1% penicillin-streptomycin solution, 10% fetal bovine serum. Specific steps:

The cells were counted using a hemocytometer and diluted with DMEM/F-12 medium to $5\times10^4$ cells/mL.

Add 100 µL of cell suspension to each well of a 96-well plate, mix, incubated at 37° C. for 24 h.

The desired test compounds were diluted to 5 concentrations: 2 mM, 0.2 mM, 20 µM, 2 µM, 0.2 µM, and 0.5 µL/well was sequentially added according to the concentration, incubated at 37° C. for 48 h.

MTT was added at a concentration of 5 mg/mL, incubated at 37° C. for 4 h.

Cells were lysed by addition of DMSO, and the OD values at 490 nm and 630 nm were measured with a microplate reader.

Processing data, calculate $IC_{50}$ value according to OD value.

Example 3. Adhesion Test of Compounds Against Human Acute Monocytic Leukemia Cells and Endothelial Cells Endothelial cell line HUVEC and human acute monocytic leukemia cell line THP-I were purchased from ATCC and cultured at 37° C. in a 5% $CO_2$ saturated humidity medium, which contains 10% fetal bovine serum, RPMI 1640 with 100 µg/mL penicillin and F-12 with 100 µg/mL streptomycin, the cells were used at logarithmic growth phase.

Polylysine (20 µg/ml) (Shanghai Yuanye Biotechnology Co., Ltd.) was coated on a black 96-well cell culture plate (Corning Incorporated costar 3603) and incubated at 37° C. for 12 h. Endothelial cells HUVECs were seeded at a concentration of $5\times10^7$ cells/well in black 96-well cell culture plates. After incubation at 37° C. for 36 h, the medium in the cell culture plates was removed. The experimental group was added with F-12 medium with 20 ng/ml TNF-α, F-12 medium without TNF-α was added to the control group, all the groups were incubated for 6 h at 37° C. At the same time, human acute monocytic leukemia cell line THP-I ($1\times10^7$ cells/well) was collected at logarithmic growth phase, and centrifuged at 1000 rpm/min for 5 mM Wash with 5 ml PBS, 1000 rpm/min, centrifuged for 5 mM, discard supernatant, add 100 µl of 1640 culture medium and 20 µM Calcein AM (Life technologies), protected from light, and incubate at 37° C. for 45 min. Centrifuged at 1000 rpm/min for 5 min, discard the supernatant, washed with 1 ml PBS, centrifuged at 1000 rpm/min for 5 min, discard the supernatant, and add 1640 medium to suspend the pellet to the desired volume. The density of to $1\times10^7$ cells/well was inoculated into a 96-well cell culture plate precoated with HUVEC cells, and different concentrations of candidate compounds were immediately added. Three replicates were set for each concentration. Only buffer was added to the control group and incubated at 37° C. for 30 min in the dark. The cell culture plate was then washed three times with PBS to remove THP-I cells that were not bound to HUVEC cells. 100 µl permeation solution (BIOSHARP) was added to each well and fluorescence was measured with a Synergy 4 Multiplate Reader (Biotek) (Ex, 485 nm; Em, 528 nm). The inhibitory effect of the candidate compound is inversely proportional to the fluorescence intensity, and the lower the fluorescence value, the stronger the inhibition effect of the compound.

SEQUENCE LISTING

<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

```
<400> SEQUENCE: 1

Ile Glu Leu Leu Gln Ala Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Ile Asp Leu Met Gln Ala Arg
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Asp Ile Thr Trp Asp Gln Leu Trp Asp Leu Met Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 4

Asp Ile Thr Trp Asp Glu Leu Trp Lys Ile Met Asn
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 5

Arg Asn Met Ser Trp Leu Glu Leu Trp Glu His Met Lys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Asp Leu Trp Asp Trp Val Val Gly Lys Pro Ala Gly
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide
<220> FEATURE:
```

-continued

```
<221> NAME/KEY: MISC_FEATURE
<222> LOCATION: (1)..(1)
<223> OTHER INFORMATION: when present in compound 9, the cystein unit
      connects to the remainder of the molecule through the SH and the
      amino group of the cystein

<400> SEQUENCE: 7

Cys Ile Glu Leu Leu Gln Ala Arg
1               5
```

What is claimed is:

1. An antitumor ternary conjugate, characterized by the following structural formula:

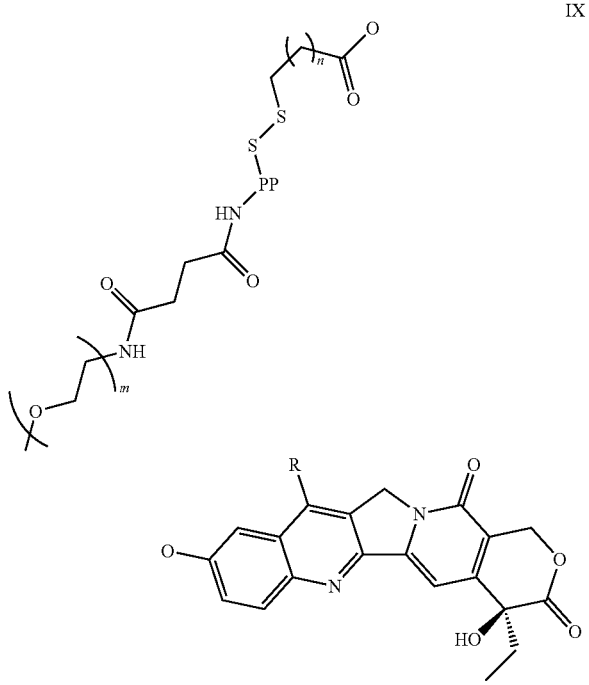

IX wherein, PP is an E-selectin peptide ligand of IELLQAR (SEQ ID NO: 1), IDLMQAR (SEQ ID NO: 2), DITWDQLWDLMK (SEQ ID NO: 3), DITWDELWKIMN (SEQ ID NO: 4), RNMSWLELWEHMK (SEQ ID NO: 5), or DLWDWVVGKPAG (SEQ ID NO: 6), which links to the remainder of the molecule through an added cysteine residue at the N-terminal; m=4-1200, n=1-3, and R is selected from hydrogen, alkyl, alkoxy, or aryl.

2. A method of treating cancer or inhibiting cancer metastasis comprising delivering the antitumor ternary conjugate of claim 1 to a tumor site.

3. An antitumor drug delivery system comprising the antitumor ternary conjugate of claim 1.

4. The antitumor drug delivery system of claim 3, wherein the antitumor ternary conjugate is present in an aqueous solution.

5. The antitumor drug delivery system of claim 3, comprising nanomicelles comprising the antitumor ternary conjugate in an aqueous solution.

6. A method of treating cancer or inhibiting cancer metastasis comprising applying the antitumor drug delivery system of claim 3 to a tumor site.

7. The antitumor ternary conjugate of claim 1, wherein R is hydrogen.

8. The antitumor ternary conjugate of claim 1, wherein PP is an E-selectin ligand of IELLQAR (SEQ ID NO: 1), which links to the remainder of the molecule through an added cysteine residue at the N-terminal.

9. An antitumor ternary conjugate having the following structure:

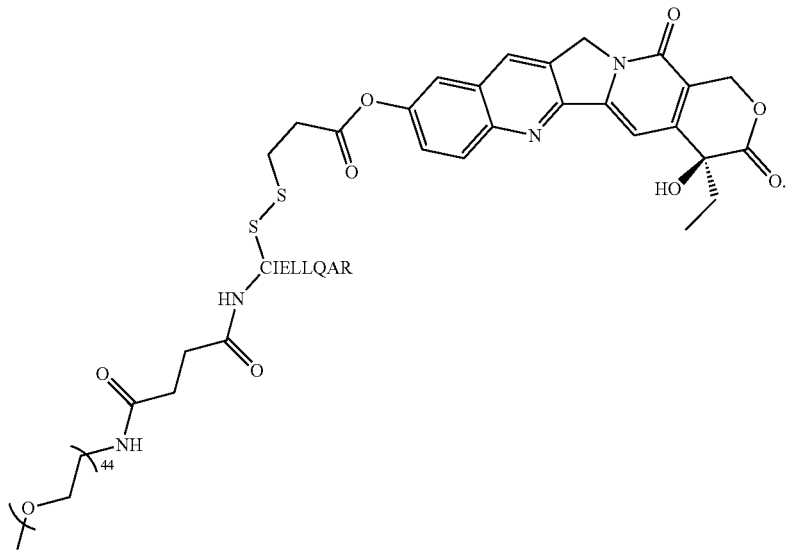

(SEQ ID NO: 7)

10. An antitumor drug delivery system comprising the antitumor ternary conjugate of claim 9.

11. The antitumor drug delivery system of claim 10, wherein the antitumor ternary conjugate is present in an aqueous solution.

12. The antitumor drug delivery system of claim 10, comprising nanomicelles comprising the antitumor ternary conjugate in an aqueous solution.

13. A method of treating cancer or inhibiting cancer metastasis comprising applying the antitumor drug delivery system of claim 10 to a tumor site.

14. A method of treating cancer or inhibiting cancer metastasis comprising delivering the antitumor ternary conjugate of claim 9 to a tumor site.

* * * * *